(12) United States Patent
Lin et al.

(10) Patent No.: US 10,138,145 B2
(45) Date of Patent: Nov. 27, 2018

(54) AIR/WATER ADVANCED OXIDATION PURIFICATION DEVICE AND SPIRAL PARTITION PLATE THEREOF

(76) Inventors: Meng Lin, Beijing (CN); Bin Lin, Beijing (CN); Xiaoduo Yu, Beijing (CN)

( * ) Notice: Subject to any disclaimer, the term of this patent is extended or adjusted under 35 U.S.C. 154(b) by 206 days.

(21) Appl. No.: 13/388,375

(22) PCT Filed: Jun. 13, 2011

(86) PCT No.: PCT/CN2011/075680
§ 371 (c)(1),
(2), (4) Date: Feb. 1, 2012

(87) PCT Pub. No.: WO2012/142784
PCT Pub. Date: Oct. 26, 2012

(65) Prior Publication Data
US 2012/0273345 A1    Nov. 1, 2012

(30) Foreign Application Priority Data
Apr. 20, 2011    (CN) .......................... 2011 1 0099385

(51) Int. Cl.
*C02F 1/32* (2006.01)
*C02F 1/461* (2006.01)
(Continued)

(52) U.S. Cl.
CPC .......... *C02F 1/46109* (2013.01); *A61L 9/205* (2013.01); *C02F 1/32* (2013.01);
(Continued)

(58) Field of Classification Search
CPC ................................ B01J 19/123; C02F 1/325
(Continued)

(56) References Cited

U.S. PATENT DOCUMENTS 3,009,409 A * 11/1961 Weaver ................ F04D 25/166
454/208
3,827,559 A * 8/1974 Gass ....................... C02F 3/082
210/150

(Continued)

FOREIGN PATENT DOCUMENTS

CN          1143730 C      3/2004
CN          1614322 A      5/2005
(Continued)

OTHER PUBLICATIONS

English translation of Chinese Office Action for Application No. 20111099385.8 dated Apr. 2, 2015.
(Continued)

*Primary Examiner* — Stefanie S Wittenberg
(74) *Attorney, Agent, or Firm* — Harness, Dickey & Pierce, P.L.C.

(57) ABSTRACT

An air/water advanced oxidation purification device includes a draft tube, a motor and at least one spiral partition plate. The spiral partition plate is fixed on an output shaft of the motor. The motor is supported in the draft tube and used for driving the spiral partition plate to rotate at uniform speed around the central axis of the draft tube and for driving air or water to enter into the draft tube. The spiral partition plate includes a plurality of miniature blades arranged along a radial direction of the spiral partition plate, each of the miniature blades includes a plurality of first and second protrusions continuously and staggered arranged along the radial direction and protruding towards two sides of the spiral partition plate, respectively. Air or water is purified through photo-catalytic advanced oxidation reaction or electro-catalytic oxidation-reduction reaction taken place on the surfaces of the spiral partition plate.

6 Claims, 6 Drawing Sheets

(51) Int. Cl.
*A61L 9/20* (2006.01)
*C02F 1/72* (2006.01)
*C02F 1/467* (2006.01)

(52) U.S. Cl.
CPC .............. *C02F 1/4672* (2013.01); *C02F 1/72* (2013.01); *C02F 2001/46123* (2013.01); *C02F 2001/46142* (2013.01); *C02F 2305/08* (2013.01); *C02F 2305/10* (2013.01)

(58) Field of Classification Search
USPC ......... 204/212; 416/176–177, 183, 185, 235, 416/236 R, 236 A
See application file for complete search history.

(56) References Cited

U.S. PATENT DOCUMENTS

| | | | | |
|---|---|---|---|---|
| 4,128,363 | A * | 12/1978 | Fujikake | F01D 5/145 416/175 |
| 5,790,934 | A * | 8/1998 | Say et al. | 422/186 |
| 5,919,422 | A * | 7/1999 | Yamanaka et al. | 422/121 |
| 6,136,203 | A * | 10/2000 | Butters et al. | 210/743 |
| 6,406,255 | B1 * | 6/2002 | Angelle | 415/121.1 |
| 2002/0172627 | A1 * | 11/2002 | Aoyagi | 422/186.3 |
| 2005/0063825 | A1 * | 3/2005 | Yang | 416/183 |
| 2009/0001027 | A1 * | 1/2009 | Carew | A01K 63/045 210/748.13 |
| 2009/0084734 | A1 * | 4/2009 | Yencho | 210/741 |
| 2010/0303679 | A1 * | 12/2010 | Kim | 422/186.3 |

FOREIGN PATENT DOCUMENTS

| | | | |
|---|---|---|---|
| CN | 201021832 Y | 2/2008 | |
| CN | 201078348 Y | 6/2008 | |
| CN | 201108806 Y | 9/2008 | |
| CN | 201301238 Y | 9/2009 | |
| CN | 202198885 U | 4/2012 | |
| DE | 3536315 A1 | 4/1987 | |
| JP | 8206668 A | 8/1996 | |
| JP | 2002307057 A | 10/2002 | |
| JP | 2004187799 | * 7/2004 | ............... A61L 9/00 |
| JP | 2008067745 A | 3/2008 | |

OTHER PUBLICATIONS

English translation of Chinese Office Action for Application No. 201110099385.8, dated Jul. 22, 2013.
International Search Report for Application No. PCT/CN2011/075680 dated Mar. 1, 2012.
International Preliminary Report for Application No. PCT/CN2011/075680 dated Oct. 22, 2013.

* cited by examiner

AIR/WATER ADVANCED OXIDATION PURIFICATION DEVICE AND SPIRAL PARTITION PLATE THEREOF

FIELD OF THE INVENTION

The invention relates to air and water purification technologies, and more particularly, to air/water advanced oxidation purification device and a spiral partition plate thereof.

BACKGROUND ART

Currently, China became the world's largest commodity production and suppliers. Development determines the expansion of production scale. However, with the expansion of production scale, air pollution is worsening. The conflict between development and pollution forces our country to find a path in which development, emission reduction and pollution treatments are coordinated and balanced. Only playing tremendous power of science and technology can make the development of our country on the path of health, green and sustainable development.

The concept of indoor air quality (IAQ) was proposed in the developed countries at the late 1970s. At that time, consideration for energy conservation, the sealing performance of housing was greatly improved. The resulting lack of indoor air resulted in the frequent occurrence of indoor pollution. U.S. scientists in the late 1980s, found in a survey that concentrations of harmful pollutants indoor are greater than that of outdoor, some greater than 100 times. Our country related department in 1984 also found in a survey that air pollution indoor in city is more serious than outdoor air, some more than outdoor 56 times. Consumers who install air conditioners are used to close doors and windows when the air conditioners work so as to reduce air conditioning loss. This requires the air conditioner manufacturers to provide the consumers with air conditioners of which the purify ability should be continuously improved.

Air purification modules (parts) chosen in the air conditioners have made progress and development in the decades. The development of the air purification modules for the air conditioners experiences roughly the following stage:

The first generation of products: humidity adjusting modules, which use the cooling dehumidification function of domestic air conditioners to adjust the indoor air humidity, but do not have air purification function.

The second generation of products: multilayer mesh modules, which use the functions of filtering, adsorption processing of the impurities of the special multilayer meshes to effectively purify suspended solids and a few harmful material in indoor air, but cannot process peculiar smell, pathogenic bacteria, viruses, microorganisms and most of organic pollutants in indoor air. Further, regular cleaning the multilayer mesh causes secondary pollutions at the same time. The biggest drawback of this technical solution is that when improving the filtering effect, the wind resistance will necessarily be increased; while reducing the wind resistance, the filtering effect will necessarily be reduced.

The third generation of products: compound air purification modules. This module increases static dust removal, electronic dust collection, anion generator, ozone generator and low temperature plasma generator on the basis of the second generation of products. The third generation of products can eliminate smoke and dust and have the functions of disinfection, sterilization, peculiar smell removal, but there still exist ills that the organic pollutants can not be effectively decomposed.

The forth generation of products: air purification modules using molecular complexation technology. This technology includes wet molecular complexation technology with adding water and dry molecular complexation technology without adding water. However, this technology also has fatal flaws: first, the service life of the molecular complex filters is only two years, if changing the molecular complex filters, this may cause the second pollution; second, specific molecular complexes can only react with certain organic matter, but there are three thousands of organic pollutants in the air, we cannot provide a kind of complex filters for each organic pollutant to solve the pollution problem.

The fifth generation of products: air purification modules using cold catalyst and photocatalytic technology. This technology is not mature enough, and is still in the theory research phase. At room temperature and atmospheric pressure, this kind of products can decompose many harmful and peculiar smell gases into smelless and harmless substance. In order to improve air purification rate, most of the manufacturers use the technical solutions of increasing the specific surface area of the cold catalyst and photocatalyst, by loading nano materials on filters of porous materials, so that the filters can be changed from pure physical absorption into absorption and decomposition at the same time. In the standard experimental test, the air purification rate of this kind of air purification modules is high in the first dozens of minutes, but is significantly reduced later; after 180 minutes, the air purification rate is too low to be acceptable. The reason is that when the filters are just opened to use, the adsorption performance of the filters is high; later, adsorption is gradually saturated, the air purification rate cannot be quickly restored to the initial level due to the lack of effective desorption.

The sixth generation of products: hydroxyl water purification modules, which adopts advanced oxidation technology to purify. The advanced oxidation technology is a hot technology in recent years, which uses hydroxyl radicals as the main antioxidant to reach with organic matter. Organic free radicals generated in the reaction can continue to participate in the chain reaction of the hydroxyl radicals, or produce further oxidative decomposition reaction after generating organic peroxide free radicals until being degraded into the final products carbon dioxide and water, thereby achieving the purpose of oxidative decomposition of organic matter. The molecular formula of hydroxyl is HO., and has a strong oxidizing property. An encapsulation equipped with hydroxyl water purification modules contains hydroxyl water of mineral water having 15 mg~60 mg/L calcium, hydroxylated mineral water can be sprayed on a surface of an evaporator to purify. The advanced oxidation reaction has high reaction speed, even to one over one million of a second.

Although the hydroxyl can cause an advanced oxidation reaction in the aqueous solution to effectively purify the water pollution, it cannot directly purify in liquid phase the three thousands of organic pollutants in gas phase. Thus, this kind of advanced oxidation technology which uses hydroxyl radicals as the main antioxidant is usually used in water purification field or air purification where environment humidity is large.

Nowadays, most of the domestic air conditioner manufacturers use only the second generation air purification technology and the third generation air purification technology. A few foreign air conditioner manufacturers use the fifth generation air purification technology and the sixth generation air purification technology, but because the technical issues are not thoroughly solved, air purification effect is not good.

Further, China is one of the countries that can be definited as the world's 13 most water-poor individuals. The shortage of water resources is one of the most outstanding problems which our country faces in the 21st century. And the water pollution situation in our country is still severe; this increases the shortage of water resources and forms a larger real threat to common people drinking water safety, economic and social sustainable development.

In order to performing advanced treatment to the reclaimed water level 1B and secondary discharged from 93% of the sewage treatment plant to achieve the reclaimed water level 1A standard so that the wastewater can be reused, thus, water can be recycled many times. The common technical solutions in domestic and foreign include: ozone oxidation, high iron oxidation and membrane separation technology.

Ozone oxidation technology: the oxidation-reduction potential of the ozone $O_3$ is 2.07V. The ozone has strong oxidation ability, and can cause the pollutants in water oxidation, decomposition, purification, bleaching, deodorization, removal of peculiar smell, sterilization, algae inhibition, disinfection. The ozone can reduce the biochemical oxygen demand (BOD) and chemical oxygen demand (COD), and eliminate surfactant bubbles. The disadvantages are that oxidative activity of the ozone has a high selectivity and it is difficult to remove the BOD and COD in the water. Meanwhile, excess ozone oxidation process will produce some by-products, of which some even have greater toxicity.

High iron oxidation technology: ferrate as non-chlorine-based efficient multi-function water treatment chemicals has a wide range of applications in water treatment field. Common ferrate includes potassium ferrate and sodium ferrate. In acidic medium, the oxidation-reduction potential of the ferrate is 2.20V, which is greater than 2.07V of the ozone, and also far greater than 1.36V the chlorine. Thus, the ferrate has high performance of oxidation, purification, bleaching, deodorization, sterilization and disinfection and other performance. Further, the ferrate has the unique function of flocculation, and can remove 80% of the suspended solids in the level 2 reclaimed water in the sewage treatment plant. The disadvantages of the high iron oxidation technology are that chemicals are needed to be added into the water, and mass production of ferrate requires a lot of energy, and also can produce a lot of pollution discharged.

Membrane separation technology: the pressure drive membrane separation process commonly used in water treatment includes micro filter, ultrafiltration, nanofiltration, etc. The advanced treatment of the reclaimed water usually adopts micro filter and ultrafiltration. Drinking water treatment adopts nanofiltration. The water quality is not affected by climate and can maintain stable. The disadvantages are that micro filter, ultrafiltration can do little about heavy metal iron pollution; meanwhile, in order to maintain the membrane permeability not to drop significantly, it must be regularly reverse pressure washed with water, causing water utilization rate reduced and waste of valuable water resources.

Today, only some of the domestic sewage treatment plants use the high iron oxidation technology, a few domestic sewage treatment plants use the membrane separation technology, most of foreign sewage treatment plants currently use the ozone oxidation technology and prepare to update for the membrane separation technology. The majority of domestic sewage water treatment plants do not do any advanced treatment to the reclaimed water which is discharged paranormally, resulting in new environmental pollution problems.

SUMMARY

In view of the above problems, the embodiment of the invention provides an air/water advanced oxidation purification device and a spiral partition plate thereof, which adopts an advanced oxidation reaction with high reaction speed to purify air, water, has the advantages of simple structure, no secondary pollution, capable of continuously performing purification, zero resistance and high purification rate for organic pollutants and viruses in air/water.

The technical solution adopted in the embodiment of the invention to solve the above technical problem is:

an air advanced oxidation purification device, comprising: a draft tube, a motor, a light source and at least one spiral partition plate, the spiral partition plate is fixed on an output shaft of the motor, and the output shaft of the motor coincides with a central axis of the draft tube, the motor is supported in the draft tube through a motor bracket, and used for driving the spiral partition plate to rotate at uniform speed around the central axis of the draft tube and for driving air to enter into the draft tube, the spiral partition plate includes a plurality of miniature blades arranged along a radial direction of the spiral partition plate, each of the miniature blades includes a plurality of protrusions arranged along the radial direction and protruding towards one side of the spiral partition plate, surfaces of the miniature blades have a plurality of layers of photocatalyst films each having aqueous layers attached thereto, and an advanced oxidation reaction takes place between the photocatalyst film and air when the photocatalyst film is irradiated by the light source.

One embodiment of the invention also provides a water advanced oxidation purification device, including: a draft tube, a motor, a constant current electrolytic power and at least one group of spiral partition plates, the motor is supported in the draft tube through a motor bracket, and used for driving the spiral partition plates to rotate at uniform speed around a central axis of the draft tube and for driving water to enter into the draft tube, each group of spiral partition plates includes an anode spiral partition plate connected to a positive electrode of the constant current electrolytic power and a cathode spiral partition plate connected to a negative electrode of the constant current electrolytic power, the anode spiral partition plate and the cathode spiral partition plate in each group of spiral partition plates are spaced from and opposite to each other, each of the anode spiral partition plate and the cathode spiral partition plate includes a plurality of miniature blades arranged along a radial direction of the spiral partition plates, each of the miniature blades includes a plurality of protrusions arranged along the radial direction of the anode spiral partition plate and the cathode spiral partition plate and protruding towards one side of the spiral partition plates, wherein water produces an oxidation reaction or advanced oxidation reaction on surfaces of the anode spiral partition plate, and produces a reduction reaction on surfaces of the cathode spiral partition plate.

One embodiment of the invention also provides a spiral partition plate including a central hole and a plurality of first miniature blades arranged along a radial direction of the spiral partition plate, each of the first miniature blades includes a plurality of first protrusions arranged along the radial direction and protruding towards one side of the spiral partition plate.

One embodiment of the invention also provides a spiral partition plate group including a plurality of spiral partition plates, every two adjacent spiral partition plates being fixed with central holes thereof being aligned;

each of the spiral partition plates includes a plurality of miniature blades arranged along a radial direction of the spiral partition plates and a fan-shape hole located between every two adjacent miniature blades, a length of the biggest outer chord of each fan-shape hole is one to two times a length of the biggest inner chord of the miniature blades.

In the air/water advanced oxidation purification device provided in one embodiment of the invention, air/water needed to be purified is guided by a motor and a draft tube through spiral partition plates which are driven to uniformly rotate by the motor, and produces a photo-catalytic advanced oxidation reaction or electro-catalytic oxidation-reduction reaction on the surfaces of the spiral partition plates, thereby achieving purification of the air/water. Since the surfaces of the spiral partition plates each have multi-layers of miniature blades having radiation shape in a radial direction which take a central hole as a centre of a circle and are uniformly distributed along a circumference direction, a plurality of layer surfaces can be formed to react with the air/water at the same time when the spiral partition plates rotate, thus, the reaction speed is high and the purification can be continuously performed.

DETAILED DESCRIPTION OF EXAMPLES

One embodiment of the invention provides an air/water advanced oxidation purification device and a spiral partition plate thereof, which adopts an advanced oxidation reaction with high reaction speed to purify air, water, has the advantages of simple structure, no secondary pollution, capable of continuously performing purification, zero resistance and high purification rate for organic pollutants in air/water.

One embodiment of the invention includes: air/water needed to be purified is guided by a motor and a draft tube through spiral partition plates which are driven to uniformly rotate by the motor, and produces a photo-catalytic advanced oxidation reaction or electro-catalytic oxidation-reduction reaction on the surfaces of the spiral partition plates, thereby achieving purification of the air/water. Since the surfaces of the spiral partition plates each have multi-layers of miniature blades having radiation shape in a radial direction which take a central hole as a centre of a circle and are uniformly distributed along a circumference direction, a plurality of layer surfaces can be formed to react with the air/water at the same time when the spiral partition plates rotate, thus, the reaction speed is high and the purification can be continuously performed.

Figure 1:
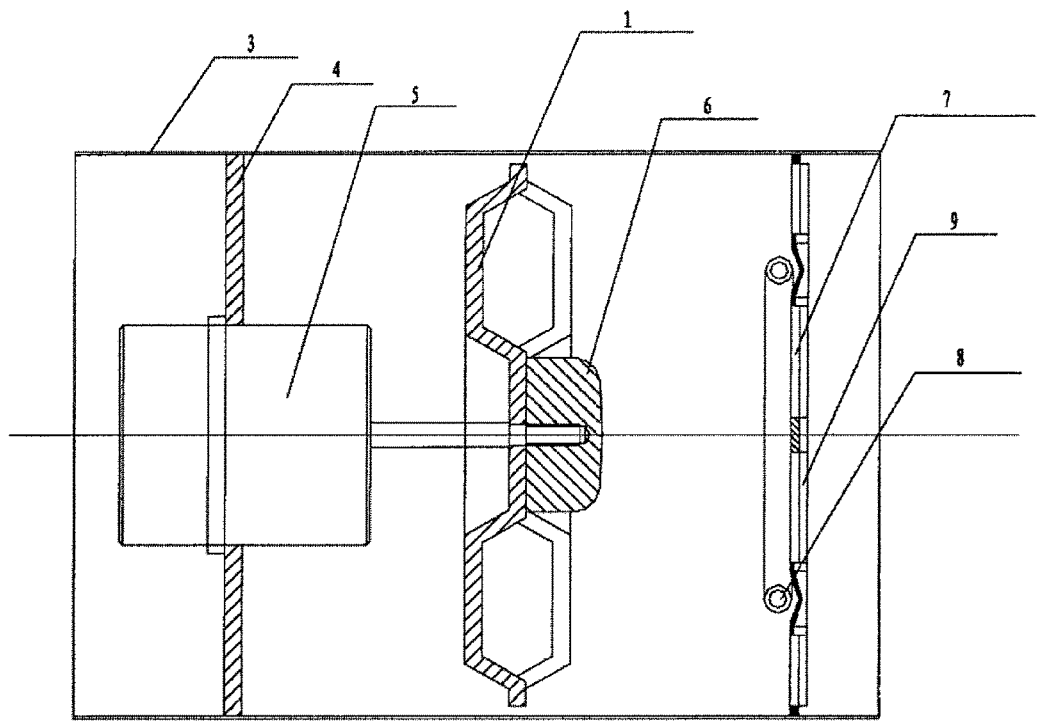
FIG. 1 is a schematic structural view of an air advanced oxidation purification device of one embodiment of the invention.

As shown in FIG. 1, an air advanced oxidation purification device provided in one embodiment of the invention includes a draft tube 3, a motor 5, a light source 8 and at least one spiral partition plate 1. The spiral partition plate 1 can be fixed on an output shaft of the motor 5, and can be fastened by a lock nut 6. The output shaft of the motor 5 can coincide with a central axis of the draft tube 3.

The motor 5 can be supported in the draft tube 3 through a motor bracket 4, and can be used for driving the spiral partition plate 1 to rotate at uniform speed around the central axis of the draft tube 3 and for driving air to enter into the draft tube 3.

Figure 2:
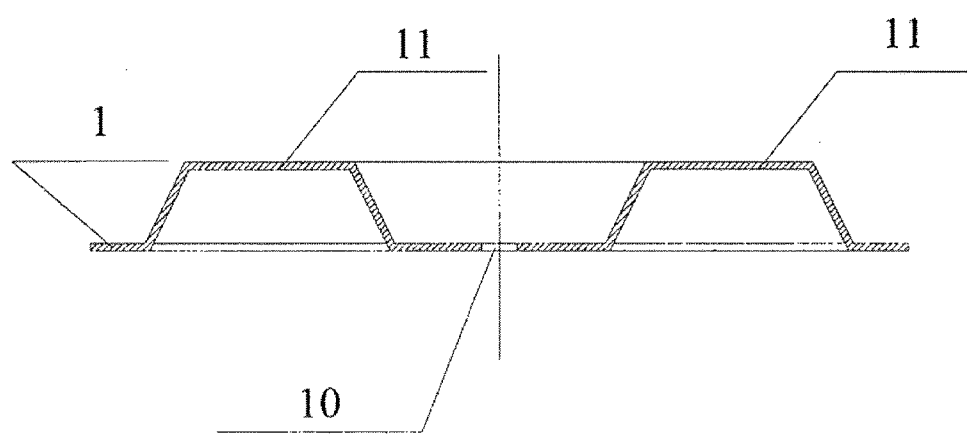
FIG. 2 is a side view of a spiral partition plate of one embodiment of the invention, which can be used in the air advanced oxidation purification device.
Figure 3:
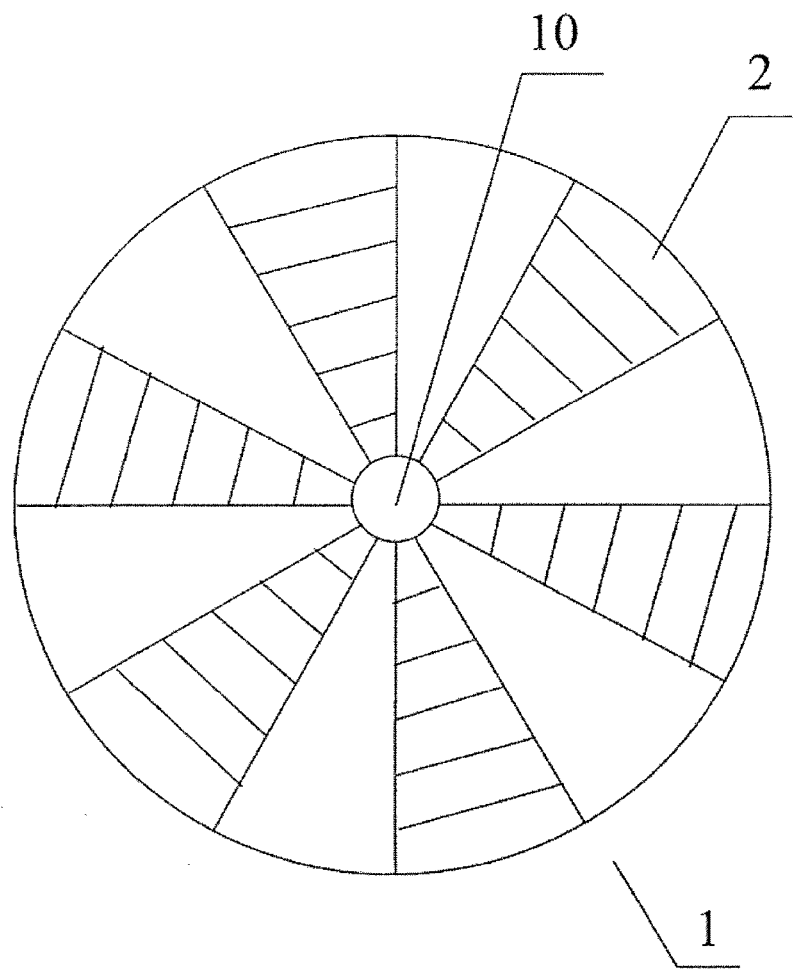
FIG. 3 is a front view of the spiral partition plate of FIG. 2.

As shown in FIGS. 2-3, the spiral partition plate 1 includes a plurality of miniature blades 2 which take a central hole 10 of the spiral partition plate 1 as a centre of a circle and are uniformly distributed along a circumference direction of the spiral partition plate 1. The miniature blade 2 is arranged along a radial direction of the spiral partition plate 1. The miniature blade 2 includes a plurality of protrusions 11 continuously arranged along the radial direction of the spiral partition plate 1. The protrusions 11 protrude towards one side of the spiral partition plate 1. The height of the protrusions 11 is in a range from 1.27 mm to 25.4 mm.

A plurality of layers of photocatalyst films each having aqueous layers are attached to the surface of the miniature blade 2. When the photocatalyst film is irradiated by the light source, an advanced oxidation reaction takes place between the photocatalyst film and air.

In order to improve the purification ability to fully perform the advanced oxidation reaction with air, the number of the spiral partition plates 1 can be in a range from 1 to 8. The spiral partition plates 1 can be fixed at one or two sides of the motor 5.

As shown in FIG. 2, preferably, the protrusion 11 can be a trapeziform protrusion, i.e., the shape of a cross-section of the protrusion 11 in the radial direction of the spiral partition plate 1 is a trapezoid. Further, an angle is defined between the protrusion and a plane of the spiral partition plate 1 and in a range from 0° to 80°.

Preferably, the miniature blades 2 can be formed in plates by stamping, drawing and laser cutting manufacturing process or precision casting process, and can be multi-layers of miniature blades having radiation shape in a radial direction which are uniformly distributed along the circumference direction, thereby forming the multi-layer spiral partition plate 1.

The spiral partition plate of the embodiment of the invention can have a variety of structures. As shown in FIGS. 2-3, in a single side of the spiral partition plate 1, one miniature blade 2 can be formed through stamping and drawing at an interval of a width of the miniature blade 2, and the protrusion direction of the protrusions 11 of each miniature blade 2 is towards the same side of the spiral partition plate 1, then this spiral partition plate can be called as single-layer spiral partition plate.

Figure 4:
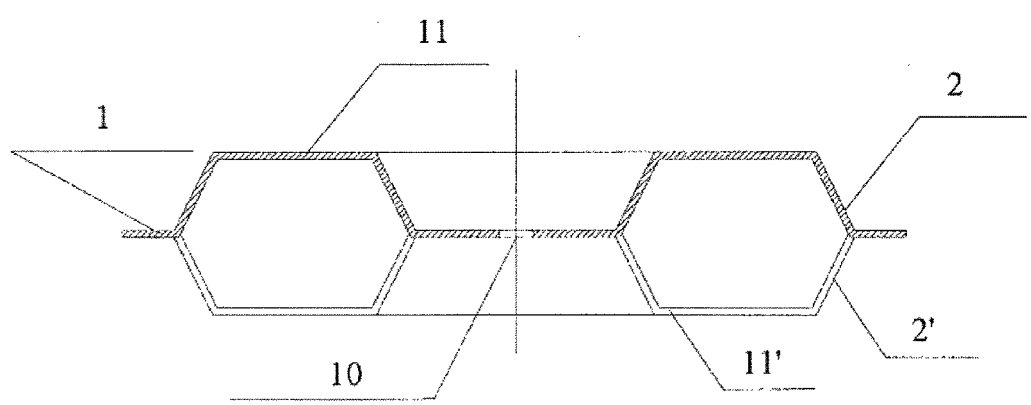
FIG. 4 is a schematic structural view of a spiral partition plate of another embodiment of the invention, which can be used in the air advanced oxidation purification device.

Or as shown in FIG. 4, the miniature blades 2 can be staggered formed in two surfaces of the spiral partition plate 1 through stamping and drawing, protrusion directions of corresponding protrusions 11, 11' of every adjacent two miniature blades: a first miniature blade 2 and a second miniature blade 2' are opposite, i.e., towards two sides of the spiral partition plate 1, respectively, thereby forming a two-layer spiral partition plate formed by two layers of the miniature blades having radiation shape in a radial direction which are uniformly distributed along the circumference direction.

Figure 5:
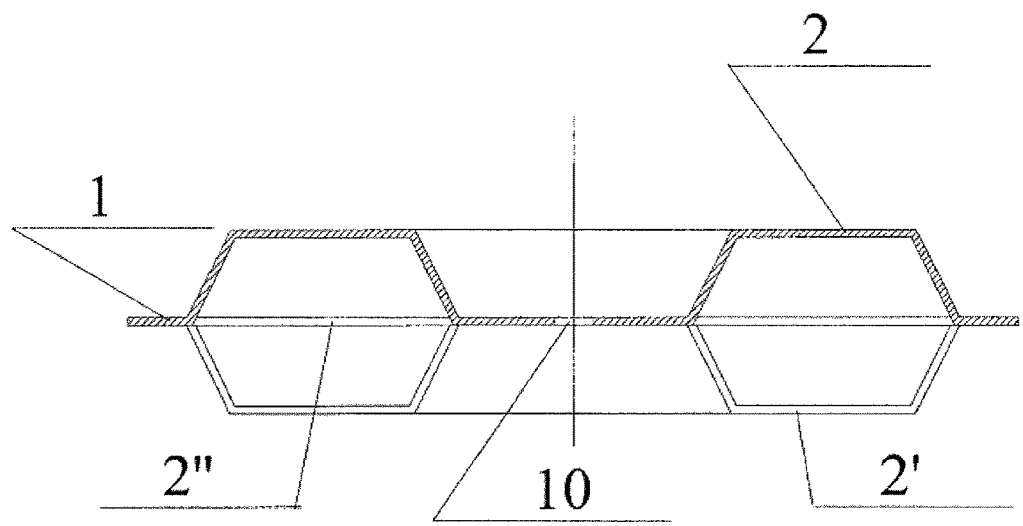
FIG. 5 is a schematic structural view of a spiral partition plate of yet another embodiment of the invention, which can be used in the air advanced oxidation purification device.

Further, as shown in FIG. 5, one first miniature blade 2 and one second miniature blade 2' can be staggered formed in two sides of the spiral partition plate 1 through stamping and drawing at an interval of the width of the miniature blade 2, i.e, a flat shaped third miniature blade 2" is further included between every two adjacent first miniature blade 2 and second miniature blade 2', thereby forming a three-layer spiral partition plate formed by three layers of miniature blades having radiation shape in a radial direction which are uniformly distributed along the circumference direction.

The multi-layer spiral partition plates as shown in FIGS. 4-5 means that the miniature blades in the surfaces of the spiral partition plate can divide the air into multi layers when the spiral partition plate rotates, so that the air can fully perform the advanced oxidation reaction with the photocatalyst films having aqueous layers attached to the surface of the miniature blades when the photocatalyst film is irradiated by the light source.

Figure 6:
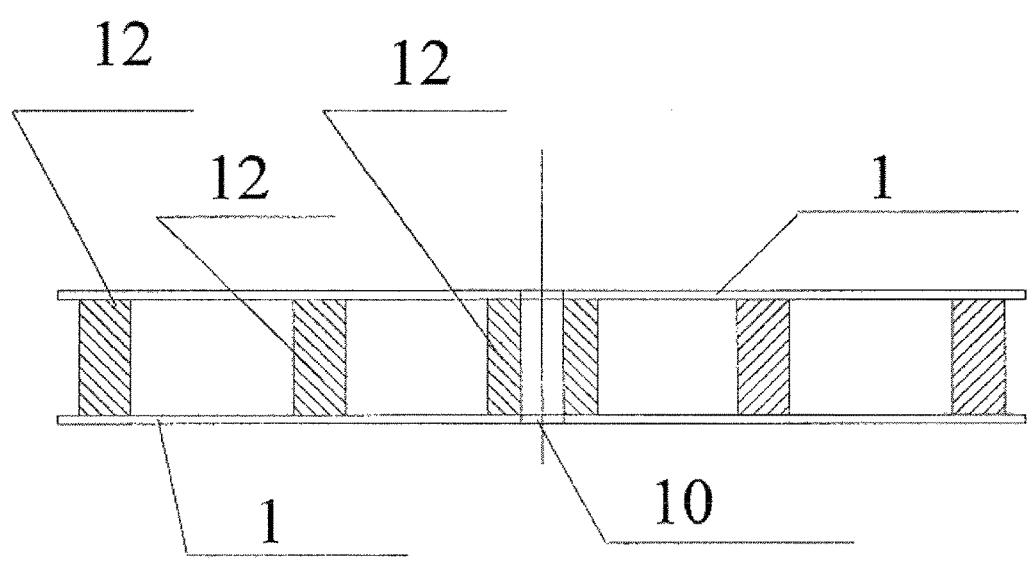
FIG. 6 is a schematic structural view of a spiral partition plate of still another embodiment of the invention, which can be used in the air advanced oxidation purification device.
Figure 7:
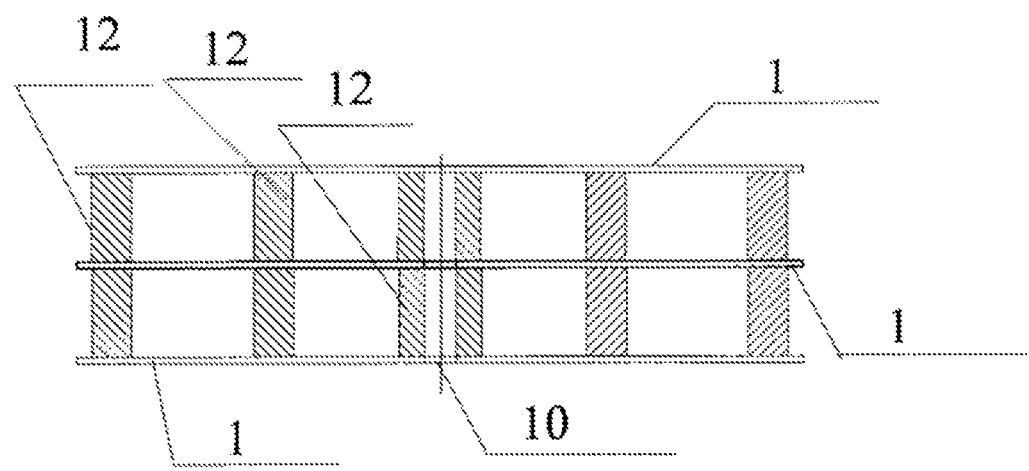
FIG. 7 is a schematic structural view of a spiral partition plate of yet still another embodiment of the invention, which can be used in the air advanced oxidation purification device.

Also as shown in FIGS. 6-7, after forming two or three single pieces of the spiral partition plate 1 from the plate through stamping die or laser cutting, a multi-layer spiral partition plate group can be formed through assembling, i.e., assembling along an axial direction the two-layer or three-layer spiral partition plates which are formed by miniature blades having radiation shape in a radial direction which take a central hole as a centre of a circle and are uniformly distributed along the circumference direction to form a two-layer or three-layer spiral partition plate group. A ring gasket 12 is fixed between two spaced spiral partition plates 1.

Like fan blades, an angle in a range from 0° to 80° can be defined between the miniature blades 2 and a plane surface of the multi-layer spiral partition plate 1, so that the miniature blades 2 can be equivalent to miniature fan blades, to increase air pressure and offset the wind resistance, so that the wind resistance of the air advanced oxidation purification device provided in the embodiment of the invention can be reduced or zero, meanwhile, some of the ultraviolet light can be reflected to a backlight portion of the spiral partition plate 1 to improve the utilization of the ultraviolet light. Relevant principles and parameters of the two-layer or three-layer spiral partition plate group formed by assembling two or three pieces of the spiral partition plates 1 along the axial direction are the same as that of the two-layer or three-layer spiral partition plates as shown in FIG. 2 or FIG. 4.

For a centrifugal fan and an axial fan, the spiral partition plates 1 can also be directly arranged on an output shaft of the motor of the fan, and the air inlet of the centrifugal fan and an air inlet or outlet of the axial fan can be used as the draft tube 3. For working conditions with low requirement for air volume and air pressure, the angle between the miniature blades 2 and the plane surface of the multi-layer spiral partition plate 1 can also be slightly increased so that the miniature blades 2 can be used as fan blades at the same time and the fan can be omitted. The air advanced oxidation purification device provided in one embodiment of the invention adopts the advanced oxidation reaction technology, has high purification rate, handles large air volume, does not add any chemicals and can be widely used for air purification and virus inactivation.

As shown in FIG. 1, the air advanced oxidation purification device provided in one embodiment of the invention further comprises a ribbon board rectifier ring 7. The ribbon board rectifier ring 7 is fixed on an inner wall of the draft tube 3. The fixed position of the ribbon board rectifier ring 7 on the inner wall of the draft tube 3 is located between two adjacent spiral partition plates 1. The ribbon board rectifier ring 7 comprises a plurality of ribbon boards 9 arranged along a radial direction of the rectifier ring. An angle is defined between the ribbon board 9 and the plane surface of the spiral partition plate 1, and the angle is in a range from 90° to 150°.

The rectifier ring 7 which uses the ribbon boards 9 as radial supporting ribs is fixed in the inner wall of the draft tube 3. A composite nano-photocatalytic film having an aqueous layer is coated on a surface of the ribbon board rectifier ring 7. When the parallel air flow in the draft tube 3 passes through the multi layers of spiral partition plates 1, the air flow direction changes accordingly from the parallel flow into a spiral flow, which results in that an efficiency of passing through the next level multi-layer spiral partition plate 1 drops drastically. By changing the angle between the ribbon board 9 and the plane surface of the multi-layer spiral partition plate 1, the spiral flow of air flow can be caused to change direction again when passing through the ribbon board 9, so that the air flow is kept to flow in a direction parallel to the center axis of the draft tube 3 to improve the work efficiency of the next level multi-layer spiral partition plate 1. The functions of the ribbon board 9 are similar to that of a stator impeller group.

Further, the light source 8 is fixed in the draft tube 3 through the ribbon board rectifier ring 7. Preferably, the light source 8 can be ultraviolet lamp.

Preferably, the air advanced oxidation purification device provided in one embodiment of the invention includes at least two spiral partition plates 1. The distance between every two adjacent spiral partition plates 1 can be in a range from 50.8 mm to 254 mm. The thickness of the miniature blades 2 can be in a range from 0.25 mm to 2.54 mm. A length of the biggest outer chord of the miniature blades 2 which is adjacent to the outer edge of the spiral partition plate is in a range from 1.27 mm to 25.4 mm, and a length of the smallest inner chord which is adjacent to the central hole of the spiral partition plate is greater than 1.1 times of the thickness of the miniature blade. The miniature blades 2 can be divided into sections in the radial direction of the spiral partition plate, and the spacing between two adjacent sections can be in a range from 1.27 mm to 50.8 mm.

The air advanced oxidation purification device provided in one embodiment of the invention uses the motor 5 to drive the multi layers of spiral partition plates 1 in the draft tube 3 to rotate at a high speed, and forces the air which contains organic pollutants and dangerous respiratory infectious virus into the draft tube at the same time. The air flow which flows at uniform speed is spirally divided into hundreds to tens of thousands of pieces of continuous spiral air film with a thickness less than 0.4 mm by hundreds to tens of thousands of the miniature blades 2 which have radiation shape in the radial direction and are uniformly distributed along the circumference direction in the one to eight multi-layer spiral partition plates 1. The composite nano-photocatalytic film having an aqueous layer is coated on a surface of each of the miniature blades 2, and can produce an advanced oxidation reaction with the organic pollutants and dangerous respiratory infectious virus contained in the air.

The air advanced oxidation purification device provided in one embodiment of the invention uses hundreds to tens of thousands of the multi-layer miniature blades, which have the composite nano-photocatalytic film having an aqueous layer coated on the surfaces thereof, and are uniformly distributed along the circumference direction and have radiation shape in the radial direction, to actively, in turn, and layer by layer close contact with each organic pollutant molecule and each virus particle which slowly migrates in the air which is forced to uniformly flow at high speed in the draft tube 3 in the movement pattern of quick spiral division, thereby the advanced oxidation reaction occurs. It fully uses the high reaction speed of one over one million of a second of photocatalysts in the advanced oxidation reaction technology, which can ensure that the air advanced oxidation purification device provided in the embodiment of the invention can eliminate the organic pollutants and completely inactivate the dangerous respiratory infectious virus in the air at high speed.

The composite nano-photocatalytic film having an aqueous layer is coated on the surface of the spiral partition plate 1, and is carried on the surfaces of the miniature blades 2. A base layer of the composite nano-photocatalytic film having an aqueous layer can be an aqueous layer of a variety of metals, metal oxides. An outer layer of the composite nano-photocatalytic film having an aqueous layer can be a titanium dioxide-based photocatalytic film, which can generate low concentration of $O_3$ and $H_2O_2$ to jointly activate the composite nano-photocatalytic film having an aqueous layer to generate a large amount of hydroxyl, which has molecular formula of HO. and has an oxidation-reduction potential of 2.8V and has such a strong oxidizing property that it can produce a chain reaction with almost all of the organic pollutants in the air until the organic pollutants are decomposed into carbon dioxide and water. Meanwhile, the dangerous respiratory infectious viruses are inactivated. The reaction time of the aforementioned advanced oxidation reaction can be one over one million seconds to one over one billion seconds. Since a straight-line distance between each of the organic pollutants and the dangerous respiratory infectious viruses in the air flow which flows at uniform speed and a divergent surface of a large amount of hydroxyl is less than 0.4 mm, this can ensure that the air advanced oxidation purification device provided in the embodiment of the invention has a high efficiency in eliminating the organic pollutants in the air and has a uniformity in inactivating the dangerous respiratory infectious viruses.

The advanced oxidation photocatalytic reactor provided in the embodiment of the invention evenly distributes individual viruses in its finite elements, i.e., the spiral air film space with a thickness of zero a few mm, and the number of collisions between each virus and HO. is the same. The number of collisions between each virus and HO. can be precisely controlled by adjusting the retention time of the virus in the advanced oxidation photocatalytic reactor and the concentration of HO..

We conclude that: the number of carbon atoms of each virus is different, and each virus should have its own constant. The number of HO. needed to kill each virus is different. The degree of decomposition of the virus can be artificially controlled by precisely adjusting the number of collisions between each $H_1N_1$ influenza virus, Corolla SARS virus and HO.. Thus, the target virus can be automatically selected from many types of viruses. This provides us with a possibility that, by precisely controlling the number of collisions between individual viruses in the advanced oxidation photocatalytic reactor and HO., it can be selected to interrupt all the carbon chain structures of the target virus to completely destroy the DNA of the target virus so that the antigenicity function of the protein and the protein fragments of the target virus can be remained on the basis of that the target virus loses pathogenicity.

Another unique feature of the advanced oxidation photocatalytic reactor provided in the embodiment of the invention is that, continuous and uniform changes can be produced to the advanced oxidation photocatalytic intensity by simple adjustments, which results in that the degree of decomposition of the virus can be artificially controlled. This provides us with a possibility, i.e., interrupting all the carbon chain structures of the virus to completely destroy the DNA of the target virus, so that on the basis of that the target virus loses pathogenicity, the protein and the protein fragments which remain the antigenicity function can quickly enter into the respiratory system to induce the immune system to produce antibodies so as to provide virus immune and protection to close contacting people in the first time. This provides a rapid and effective prevention device for controlling the virus of constant mutation.

At the room temperature, atmospheric pressure, the migration rate of particulars of a diameter of 0.1 microns caused by Brownian motion of gas molecules collision is only 37 microns per second. A variety of advanced oxidation devices except for the advanced oxidation purification device provided in the embodiment of the invention, in a large scale space, cannot make each virus particle to uniformly collide with hydroxyls of slow migration of diffusion which are generated by the nano-photocatalytic film having an aqueous layer which is on fixed carriers, and can not continuously and uniformly change the concentration of the hydroxyls, and cannot precisely control the numbers of collisions between individual viruses and HO., and cannot be used for continuous preparation of viral antigens.

The aforementioned membrane-type advanced oxidation reaction is a comparatively perfect purification technology at present, thus the reaction process is not repeated here.

The advantages of the air advanced oxidation purification device provided in the embodiment of the invention are that: it fully uses the high reaction speed of one over one million of a second of photocatalysts of titanium dioxide, ultraviolet ray, ozone, hydrogen peroxide, metal oxide and metal ions with the aqueous layer in the advanced oxidation reaction technology, to spirally divide the air flow which flows at uniform speed into hundreds to tens of thousands of pieces of continuous spiral air films with a thickness less than 0.4 mm by hundreds to tens of thousands of the miniature blades which have the composite nano-photocatalytic film having the aqueous layer attached to the surfaces thereof, and are uniformly distributed along the circumference direction and have radiation shape in the radial direction in the spiral partition plates. Comparing an actual contact area between a composite nano-photocatalytic film having an aqueous layer attached to an inner wall of a draft tube and an air flow which flows at uniform speed, to an actual contact area between the hundreds to tens of thousands of pieces of continuous spiral air films with a thickness less than 0.4 mm which is spirally divided from an air flow which flows at uniform speed by hundreds to tens of thousands of multi layers trapezoidal regions and the composite nano-photocatalytic film having an aqueous layer, the actual contact area between the air and the composite nano-photocatalytic film having the aqueous layer of the air advanced oxidation purification device provided in the embodiment of the invention is greater than 4000 times.

In order to perform an objective standard comparison of the performances of various kinds of different air purification devices adopting the advanced oxidation technology, the equivalent specific surface area calculation method can be used to analysis the performances. It defines: in a certain time such as one second; at certain air speed such as three meters per second; in a certain volume such as an air purification device of 1 cubic meters, an actual area between surfaces coated with the composite nano-photocatalytic film having an aqueous layer and the air is how many square meters per second, then the equivalent specific surface area is how many square meters per second.

According to the equivalent specific surface area calculation method, in the conditions that the time is 1 second, the air speed is 3 meters per second, and the volume of equipment is 1 cubic meters:

Situation A: four walls coated with PHI film, length*width*height=1 meter*1 meter*1 meter=1 cubic meters ventilation pipe of a central air-conditioning. An actual windward perimeter of the composite nano-photocatalytic film having the aqueous layer coated on the surfaces of the four walls is 4 meters, and when the air speed is 3 meters per second, an actual area between the air and the composite nano-photocatalytic film having the aqueous layer is 4 meter*3 meters per second=12 square meters per second, i.e., the equivalent specific surface area is 12 square meters per second.

Situation B: in an air advanced oxidation purification device of 1 cubic meters provided in the embodiment of the invention, 8000 pieces of multi-layer miniature blades can be included. A length of each miniature blade can be about 0.4 meters. Since two surfaces of the miniature blade are coated with the composite nano-photocatalytic film having the aqueous layer, thus when dividing the air, the actual windward side length is doubled and the total windward length is 0.4 meters*8000*2=6400 meter. The average linear velocity of the spiral partition plate is 7.5 meters per second. An actual area between the air and the composite nano-photocatalytic film having the aqueous layer is 6400 meter*7.5 meters per second=48000 square meters per second, i.e., the equivalent specific surface area is 48000 square meters per second. The equivalent specific surface area obtained in the situation B is 4000 times of the equivalent specific surface area obtained in the situation A.

That is to say, if air purification devices of the same volume adopt the advanced oxidation technology, in equal time, the air advanced oxidation purification device provided in the embodiment of the invention can increase the actual area between the air and the composite nano-photocatalytic film having the aqueous layer by 4000 times, and can reduce the maximum distance between all the organic pollutants and the dangerous respiratory infectious viruses in the air flow which flows at uniform speed in a duct having a section of 1 meter*1 meter and the composite nano-photocatalytic film having the aqueous layer from 500 mm to below 0.4 mm, i.e, reducing by more than 1000 times. Every reducing the distance by one time, the concentration of the hydroxyls will be accordingly increased by 8 times.

In existing filtering methods, in order to filter the viruses, the efficient filter HEPA having big volume and big air resistance has to be chosen. The gap of the HEPA which is made of super-thinness glass fiber and PP material can be small to 0.1 microns. But in order to keep ventilation rate unchanged, it must be changed frequently or cleaned many times in addition to the requirement of increasing the air pressure. The ventilated area of each trapezoidal hole of the multi-layer spiral partition plate of the embodiment of the invention is greater than hundreds of hundred million times the gap of 0.1 microns of the HEPA, and the air resistance is very small. Further, the final products of the advanced oxidation technology are carbon dioxide and water, and there is no secondary pollution and there is no need for cleaning and maintenance.

Figure 8:
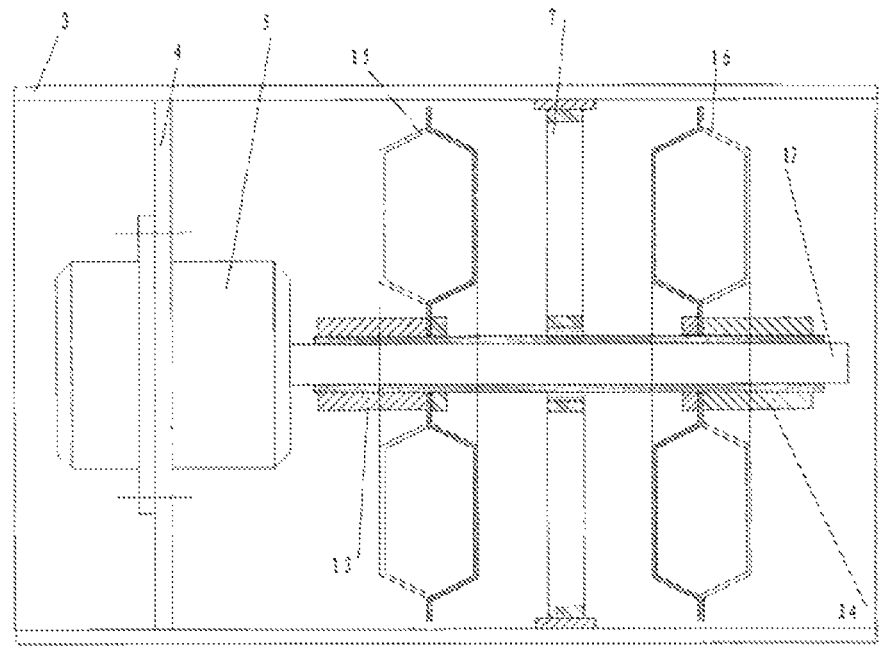
FIG. 8 is a schematic structural view of a water advanced oxidation purification device of one embodiment of the invention.

One embodiment of the invention also provides a water advanced oxidation purification device. As shown in FIG. 8, the water advanced oxidation purification device provided in the embodiment of the invention includes a draft tube 3, a motor 5, a constant current electrolytic power and at least one group of spiral partition plates. The motor 5 can be supported in the draft tube 3 through a motor bracket 4, and can be used for driving the spiral partition plates to rotate at uniform speed around the central axis of the draft tube 3 and for driving water to enter into the draft tube 3.

Each group of spiral partition plates includes an anode spiral partition plate 16 connected to a positive electrode of the constant current electrolytic power and a cathode spiral partition plate 15 connected to a negative electrode of the constant current electrolytic power. The anode spiral partition plate 16 and the cathode spiral partition plate 15 in each group of spiral partition plates are spaced from and opposite to each other.

The structure of each of the anode spiral partition plate 16 and the cathode spiral partition plate 15 can be the same as that of the spiral partition plate 1 or the spiral partition plate group shown in FIGS. 2-7, and includes a plurality of miniature blades 2 which take a central hole 10 as a centre of a circle and are uniformly distributed along a circumference direction, respectively. The miniature blades 2 are arranged along a radial direction of the anode spiral partition plate 16 and the cathode spiral partition plate 15, respectively. The miniature blade 2 includes a plurality of protrusions arranged along the radial direction and protruding towards one side of the anode spiral partition plate 16 or the cathode spiral partition plate 15. Water produces an oxidation reaction or advanced oxidation reaction on the surface of the anode spiral partition plate 16, and produces a reduction reaction on the surface of the cathode spiral partition plate 15.

The water advanced oxidation purification device provided in the embodiment of the invention further comprises at least one ribbon board rectifier ring 7. The ribbon board rectifier ring 7 is fixed on an inner wall of the draft tube 3. Each ribbon board rectifier ring 7 is located between the anode spiral partition plate 16 and the cathode spiral partition plate 15 of each group of the spiral partition plates.

The ribbon board rectifier ring 7 includes a plurality of ribbon board 9 such as trapezoidal leaves arranged along a radial direction of the rectifier ring. An angle is defined between the ribbon board 9 and a plane surface of the anode spiral partition plate 16 or the cathode spiral partition plate 15. The angle between the ribbon board 9 and the plane surface of the anode spiral partition plate 16 or the cathode spiral partition plate 15 is in a range from 90° to 150°.

Preferably, each anode spiral partition plate 16 is connected to a positive electrode of the constant current electrolytic power through a positive current collector ring 14. Each cathode spiral partition plate 15 is connected to the negative electrode of the constant current electrolytic power through a negative current collector ring 13.

The number of the spiral partition plates can be one group to eight groups which can be fixed at one or two sides of the motor 5 in pairs opposite to one another. The distance between every two adjacent anode spiral partition plate 16 and cathode spiral partition plate 15 can be in a range from 2.54 mm to 254 mm. The thickness of the spiral partition plate can be in a range from 0.25 mm to 5.08 mm. The miniature blades 2 can have electrode materials coated on surfaces thereof or can be made of electrode materials. The miniature blade 2 has a length of the biggest outer chord which is adjacent to the outer edge of the spiral partition plate in a range from 1.27 mm to 50.8 mm, and a length of the smallest inner chord which is adjacent to the central hole of the spiral partition plate greater than 1.1 times of the thickness of the miniature blade. The miniature blades 2 can be divided into sections in the radial direction of the spiral partition plate, and the spacing between two adjacent sections can be in a range from 1.27 mm to 50.8 mm.

The water advanced oxidation purification device provided in the embodiment of the invention arranges at least one electrocatalysis anode multi-layer spiral partition plate 16, at least one electrocatalysis cathode multi-layer spiral partition plate 15, at least one positive current collector ring 14, and at least one negative current collector ring 13 on a motor shaft 12 in a draft tube 3. The anode multi-layer spiral partition plate 16 and the cathode multi-layer spiral partition plate 15 are insulated arranged along the axial direction, and are interposed with the ribbon board rectifier ring 7 which is insulated fixed on an inner wall of the draft tube 3.

If only processing source water in which heavy metal ions exceed bid, the insulated fixed ribbon board rectifier ring 7 can also be used as an anode, and the multi-layer spiral partition plates can be used as a cathode, to be connected to the positive electrode and the negative electrode of the constant current electrolytic power, respectively. The insulated fixed ribbon board rectifier ring 7 can also be used as a third electrode, so that the water advanced oxidation purification device provided in the embodiment of the invention becomes a three-dimensional reactor device which can select the appropriate modified electrode to improve purification efficiency. The functions of the ribbon board rectifier ring 7 are the same as that of the ribbon board rectifier ring of the air advanced oxidation purification device provided in the embodiment of the invention, and are not repeated here.

If the water quality of the reclaimed water is deteriorated due to weather and climate changes, an on-line measurement instrument can be selected to monitor pollution changes in the reclaimed water, and strength of the current output of the constant current electrolytic power can be adjusted by an automatic control unit to automatically adjust the intensity of electro-catalytic oxidation reaction. This can not only save power but also ensure the quality of the advanced treatment of the reclaimed water. Gas leading slots can be arranged in the top of the draft tube 3 to guide oxygen exhalation in the anode multi-layer spiral partition plate 16 and hydrogen exhalation in the cathode multi-layer spiral partition plate 15 out. The hydrogen exhalation can be used as a new energy after purification.

When a diameter of the multi-layer spiral partition plate is less than 2 meters, the draft tube 3 can be selectively arranged horizontally. If a diameter of the multi-layer spiral partition plate is greater than 2 meters, the draft tube 3 can be selectively arranged vertically. The multi-layer spiral partition plate can be formed through assembling along the axial direction multi layers of the spiral partition plates which are formed by trapezoidal regions having radiation shape in a radial direction which are uniformly distributed along the circumference direction.

Similar to the air advanced oxidation purification device, the manufacturing method of the anode spiral partition plate 16 and the cathode spiral partition plate 15 uses stamping and laser cutting manufacturing process or precision casting process to form miniature blades 2 having radiation shape in a radial direction which are uniformly distributed along the circumference direction in the plate formed by pressing electrode materials. An angle can be defined between the miniature blades 2 and a plane surface of the anode spiral partition plate 16 or the cathode spiral partition plate 15. The miniature blades 2 can be equivalent to axial flow micro turbine blades, to increase the thrust on water flowing in the draft tube 3, so that the water resistance of the water advanced oxidation purification device provided in the embodiment of the invention can be reduced or zero. For a centrifugal drainage machine and an axial drainage machine, the spiral partition plates can also be directly arranged on an output shaft of the motor of the drainage machine, and the water inlet of the centrifugal drainage machine and the axial drainage machine can be used as the draft tube 3. For working conditions with low requirement for water volume and water pressure, the angle between the miniature blades 2 and the plane surface of the multi-layer spiral partition plate can also be slightly increased so that the miniature blades 2 can be used as drainage machine blades and the drainage machine can be omitted.

The water advanced oxidation purification device provided in the embodiment of the invention adopts the electrocatalytic oxidation-reduction technology in the advanced oxidation reaction technology, has high purification rate, handles large water volume, does not add any chemicals and can be used for advanced treatment of the reclaimed water in the sewage treatment plant and for heavy metal pollution purification treatment in the water plant, and can be widely used in water purification for family, enterprise and city.

The spiral partition plate of the water advanced oxidation purification device provided in the embodiment of the invention can have a variety of structures, and all the aforementioned spiral partition plates for the air purification can be used as anode multi-layer spiral partition plate 16 and the cathode multi-layer spiral partition plate 15. Further, the manufacturing method of the anode multi-layer spiral partition plate 16 and the cathode multi-layer spiral partition plate 15 can be: using stamping die or laser cutting to form single pieces of one over thirty to half of single piece of the spiral partition plate which is then assembled into one complete single piece of the spiral partition plate, and assembling two to twelve layers of single pieces of the spiral partition plates into two-layer or twelve-layer anode multi-layer spiral partition plate group or cathode multi-layer spiral partition plate group. That is, the two-layer or twelve-layer anode multi-layer spiral partition plate or cathode multi-layer spiral partition plate is formed by two-layers of or twelve-layers of miniature blades having radiation shape in a radial direction which take a central hole 10 as a centre of a circle and are uniformly distributed along the circumference direction.

Figure 9:
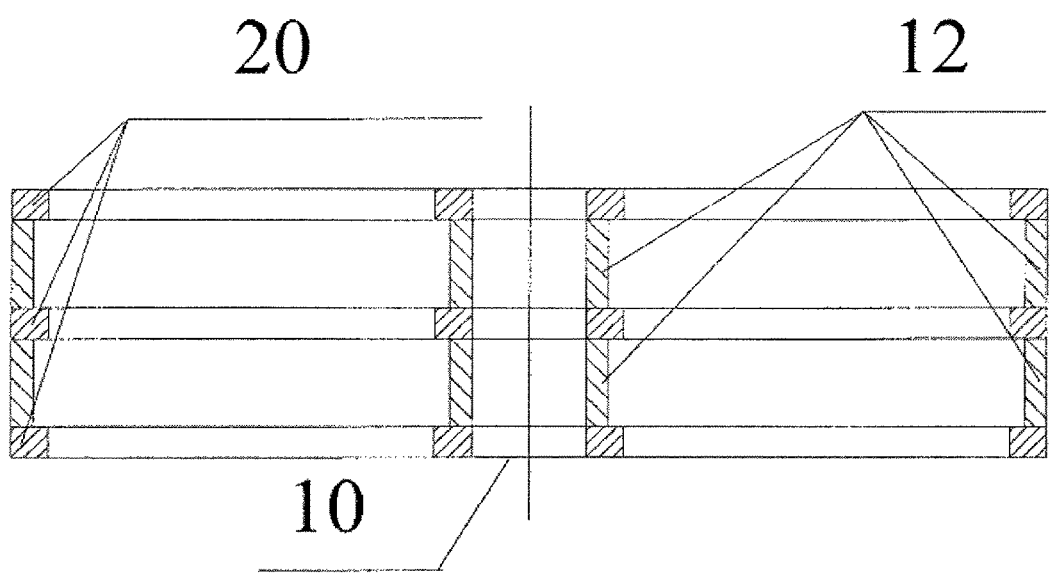
FIG. 9 is a schematic structural view of a spiral partition plate of one embodiment of the invention, which can be used in the water advanced oxidation purification device.
Figure 10:
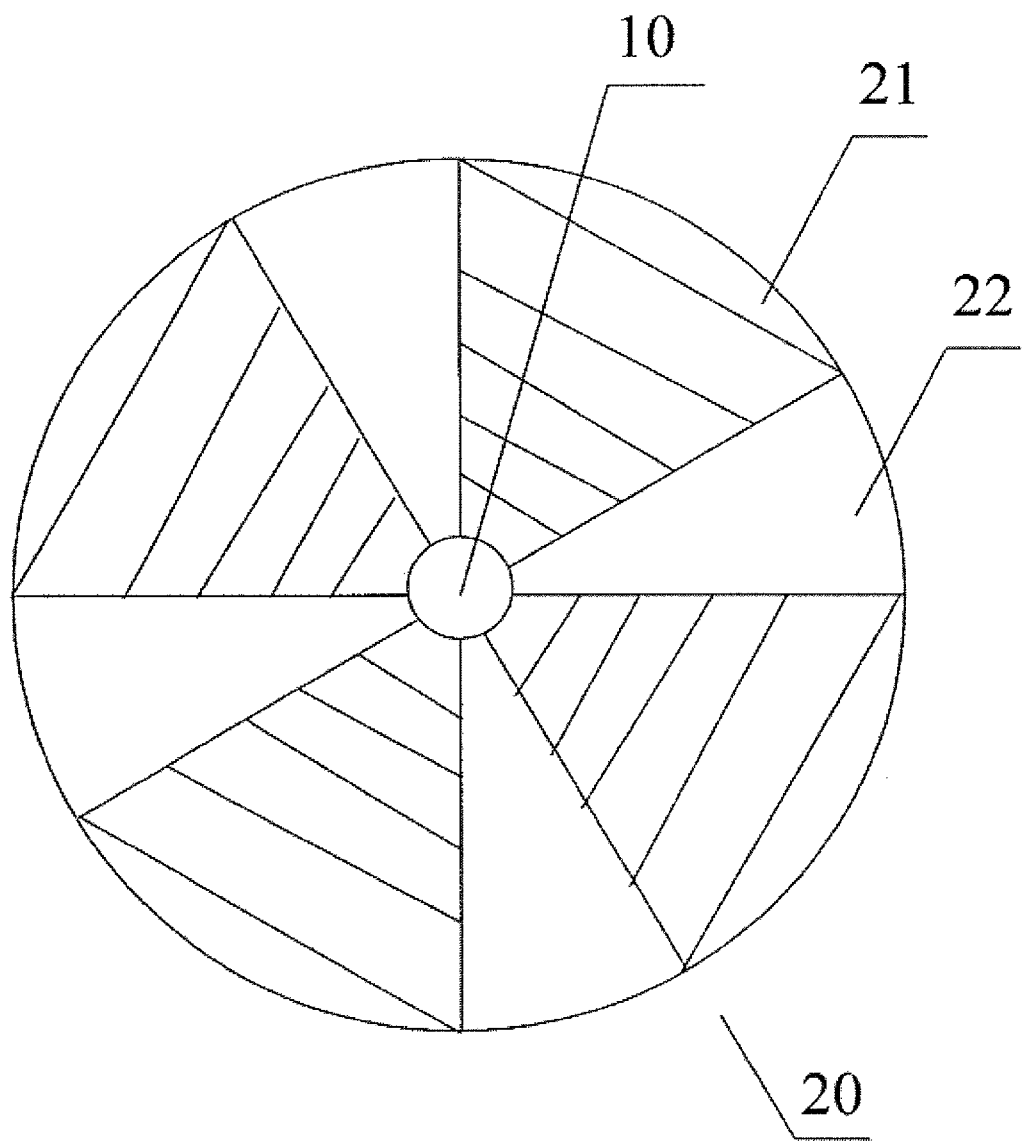
FIG. 10 is a schematic structural view of a spiral partition plate of another embodiment of the invention, which can be used in the water advanced oxidation purification device.

Or, the spiral partition plate group for the air/water advanced oxidation purification device provided in the embodiment of the invention can use another kind of form. As shown in FIGS. 9-10, a plurality of fan-shape holes 21 having the shape of the miniature blades can be formed in a single side of the spiral partition plate 20 and take the central hole 10 as a centre of a circle through stamping mould punching or laser cutting. One piece of the miniature blade can be formed between two adjacent fan-shape holes 21. A length of the biggest outer chord of each fan-shaped hole 21 is one or two times the length of the biggest inner chord of the miniature blade 22, thereby forming a spiral partition plate component formed by miniature blades 22 having radiation shape in a radial direction which take the central hole 10 as a centre of a circle and are uniformly distributed along the circumference direction. The spiral partition plate component is one over thirty to half of single piece of the spiral partition plate. A plurality of spiral partition plate components can be assembled into one complete single piece of the spiral partition plate. Two to twelve layers of single pieces of the spiral partition plates can be assembled along the axial direction into two-layer or twelve-layer anode multi-layer spiral partition plate group or cathode multi-layer spiral partition plate group. That is, the two-layer or twelve-layer anode multi-layer spiral partition plate or cathode multi-layer spiral partition plate is formed by two-layers of or twelve-layers of miniature blades having radiation shape in a radial direction which take the central hole 10 as a centre of a circle and are uniformly distributed along the circumference direction.

Stamping plastic mold can be used to form an angle between the miniature blades 22 of the spiral partition plate component and a plane surface of the anode multi-layer spiral partition plate 16 or the cathode multi-layer spiral partition plate 15 and to assembly a plurality of spiral partition plate components into one complete single piece of the spiral partition plate 20. Then, two to twelve layers of single pieces of the spiral partition plates can be assembled along the axial direction into two-layer or twelve-layer anode multi-layer spiral partition plate 16 or cathode multi-layer spiral partition plate 15 formed by two-layers of or twelve-layers of miniature blades having radiation shape in a radial direction which are uniformly distributed along the circumference direction. A plurality of ring gaskets 12 can be used between every two single pieces of the spiral partition plates 20 to fix axial distance. The distance between every two adjacent spiral partition plates 20 can be in a range from 2.54 mm to 50.8 mm.

Further, an angle difference between the corresponding fan-shaped holes of every two adjacent spiral partition plates 20 can be the radian of the miniature blade 22. That is, relative to the adjacent spiral partition plate 20, each spiral partition plate 20 has a rotation angle which can be the radian of the miniature blade 22.

The water advanced oxidation purification device provided in the embodiment of the invention uses the motor to drive the anode multi-layer spiral partition plates and the cathode multi-layer spiral partition plates in the draft tube to rotate at uniform speed, and forces the reclaimed water or heavy metal pollution source water into the draft tube at the same time. The water flow which flows at uniform speed is spirally divided into hundreds to tens of thousands of pieces of continuous spiral water film with a thickness less than 0.4 mm by hundreds to tens of thousands of the miniature blades which have radiation shape in the radial direction and are uniformly distributed along the circumference direction in one to eight anode spiral partition plates and one to eight cathode spiral partition plates. The multi-layer spiral partition plates of the water advanced oxidation purification device provided in the embodiment of the invention can be used as movement electrodes. The multi-layer spiral partition plates can be used as multi-layers of miniature blade electrodes in the movement pattern of quick spiral division, and actively, in turn, and layer by layer close contact with each organic pollutant molecule and each heavy metal iron which slowly migrates in the water, to generate an electro-catalytic oxidation-reduction reaction. The organic pollutants in the water films with a thickness less than 0.4 mm produces a direct oxidation reaction with the surfaces of the anode spiral partition plates, or produces an indirect oxidation reaction with its surrounding HO. which has strong oxidizing property. HO. has an oxidation-reduction potential of 2.8V, which is greater than the oxidation-reduction potential of the commonly used potassium ferrate and natrium ferrate, 2.20V, greater than the oxidation-reduction potential of ozone, 2.07V and is also far greater than the oxidation-reduction potential of chlorine, 1.36V. The water advanced oxidation purification device provided in the embodiment of the invention has a higher oxidation, purification, bleaching, deodorization, sterilization, disinfection and other performance. The final products of the advanced oxidation technology are carbon dioxide and water. The heavy metal irons in the water films with a thickness less than 0.4 mm produces a cathodic reduction reaction with the surfaces of the cathode spiral partition plates to reduce the heavy metal irons to metal which is deposited on the surfaces of the cathode spiral partition plates, thereby achieving the purpose of recovering metal and eliminating water pollution. In water, the migration rate of the charged particulars in the electric field is only 30-40 microns per second, except for the organic pollutants and the heavy metal irons in the laminar flow close to the electrode surface, most of the rest cannot participate in the oxidation-reduction reaction in short time. For example, when processing in an airtight static pool of 10 meters, it will take 60-80 hours to thoroughly complete the electro-catalytic oxidation-reduction reaction. Thus, the electro-catalytic oxidation-reduction reaction process cannot be used for advanced treatment of heavy metal iron exceeding bid pollution of the reclaimed water and the source water in large volume. If using mesh electrodes, the metal reduced from the heavy metal iron will be deposited on the metal mesh, and the meshes will soon be blocked and cannot work.

The advantages of the water advanced oxidation purification device provided in the embodiment of the invention are that: it fully uses the technical characteristics of high reaction speed of the electro-catalytic oxidation-reduction reaction. The water flow which flows at uniform speed in the draft tube is spirally divided into hundreds to tens of thousands of pieces of continuous spiral water films with a thickness less than 0.4 mm by hundreds to tens of thousands of the multi-layer miniature blades which are uniformly distributed along the circumference direction and have radiation shape in the radial direction in the anode spiral partition plates and the cathode spiral partition plates. The straight-line distances between the organic pollutants, the heavy metal iron in the water films and the anode surface or the cathode surface, respective, are less than 0.4 mm, thus the oxidation-reduction reaction can quickly occur. The hydrogen exhalation in the cathode spiral partition plates can be used as a new energy after being guided out and being purified. Meanwhile, an area of each fan-shaped hole in the spiral partition plates is nearly a thousand times larger than that of the mesh of the mesh electrodes, thus, the spiral partition plates have a small water resistance; further, the spiral partition plates are flushed with high-speed water, and are not easy to be blocked.

The foregoing are only preferred embodiments of the invention and are not for use in limiting the protection scope thereof. All modifications, equivalent replacements or improvements in accordance with the spirit and principles of the invention shall be included in the protection scope of the invention.

The invention claimed is:

1. A planar partition plate for an advanced oxidation purification device, the planar partition plate comprising;
   a central hole and a plurality of first miniature blades arranged intermittently around a circumference of and along a radius of the planar partition plate, wherein the planar partition plate is fixed on an output shaft of a motor through the central hole;
   each of the first miniature blades includes a first planar protrusion arranged along the respective radius and protruding away from one side of the planar partition plate and arranged in a plane substantially parallel to the planar partition plate;
   wherein the planar partition plate further comprises a plurality of second miniature blades formed from a planar portion of the planar partition plate, arranged intermittently around a circumference of and along a respective radius of the planar partition plate, each of the second miniature blades includes a second planar protrusion formed from a planar portion of the planar partition plate and, arranged along the respective radius of the planar partition plate and in the plane substantially parallel to the partition plate, and protruding away from an opposite side of the planar partition plate from the first protrusion,
   wherein the first miniature blades and the second miniature blades are arranged in a staggered, alternating configuration;
   wherein surfaces of each of the first and second miniature blades have a plurality of layers of photocatalyst films each having aqueous layers attached thereto,
   wherein each of the photocatalyst films is configured to produce an advanced oxidation reaction with air flowing past the each of the photocatalyst films when the each of the photocatalyst films is irradiated by light; and
   wherein the first and second miniature blades divide air flowing through the planar partition plate into multiple continuous air layers with a thickness less than 0.4 mm when the motor drives the planar partition plate to rotate;
   wherein each of the first and second miniature blades includes an outer chord connecting to an outer edge of the partition plate and an inner chord connecting to an inner edge of the partition plate, and a length of the outer chord is in a range from 1.27 mm to 25.4 mm, and a length of the inner chord is greater than 1.1 times of a thickness of each of the first and second miniature blades.

2. The planar partition plate of claim 1, further comprising a plurality of third miniature blades, each of the third miniature blades is located between one of the first miniature blades which is adjacent to the each of the third miniature blades and one of the second miniature blades which is adjacent to the each of the third miniature blades.

3. The planar partition plate of claim 2, wherein a thickness of the first, second and third miniature blades is in a range from 0.25 mm to 5.08 mm.

4. The planar partition plate of claim 3, wherein an angle defined between each of the first, second and third miniature blades and a plane of the planar partition plate is in a range from 0° to 80°.

5. The planar partition plate of claim 1, wherein the first and second protrusions have a height in a range from 1.27 mm to 25.4 mm.

6. A planar partition plate group for an advanced oxidation purification device, the planar partition plate group comprising a plurality of planar partition plates,
   at least one planar partition plate including a central hole and a plurality of first miniature blades formed from a planar portion of the planar partition plate and arranged intermittently around a circumference of and along a respective radius of the planar partition plate and each of the planar partition plates is fixed on an output shaft of a motor through its central hole;
   every two adjacent planar partition plates being fixed relative to each other with central holes thereof being aligned;
   each of the first miniature blades includes a first protrusion arranged along the respective radius of the planar partition plate and protruding away from one side of the planar partition plate and arranged in a plane substantially parallel to the planar partition plate;
   wherein the planar partition plate further includes a plurality of second miniature blades formed from a planar portion of the planar partition plate and arranged intermittently around a circumference of and along a respective radius of the planar partition plate, each of the second miniature blades includes a second protrusion arranged along the respective radius and protruding away from an opposite side of planar partition plate from the first protrusion and arranged in a plane substantially parallel to the planar partition plate, wherein the first miniature blades and the second miniature blades are arranged in a staggered configuration;
   wherein surfaces of each of the first and second miniature blades have a plurality of layers of photocatalyst films each having aqueous layers attached thereto; wherein each of the photocatalyst films is configured to produce an advanced oxidation reaction with air flowing past the each of the photocatalyst films when the each of the photocatalyst films is irradiated by light; and
   wherein the first and second miniature blades divide air flowing through the planar partition plate into multiple continuous air layers with a thickness less than 0.4 mm when the motor drives the planar partition plate to rotate;
   wherein each of the first and second miniature blades includes an outer chord connecting to an outer edge of the partition plate and an inner chord connecting to an inner edge of the partition plate; a length of the outer chord is in a range from 1.27 mm to 25.4 mm, and a length of the inner chord is greater than 1.1 times of a thickness of each of the first and second miniature blades.

* * * * *